(12) United States Patent
Yu et al.

(10) Patent No.: US 7,748,256 B2
(45) Date of Patent: Jul. 6, 2010

(54) NONDESTRUCTIVE TESTING OF TORSIONAL VIBRATION DAMPERS

(75) Inventors: Linxiao Yu, Peoria, IL (US); Douglas A. Rebinsky, Peoria, IL (US); Dong Fei, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 343 days.

(21) Appl. No.: 11/825,013

(22) Filed: Jul. 3, 2007

(65) Prior Publication Data

US 2009/0007629 A1 Jan. 8, 2009

(51) Int. Cl.
 *G01N 11/02* (2006.01)
 *G01N 11/10* (2006.01)
(52) U.S. Cl. .................. 73/53.05; 73/54.01; 73/54.15
(58) Field of Classification Search ............. 73/53.05, 73/54.01, 54.15, 54.41, 865.6, 865.8, 865.9
See application file for complete search history.

(56) References Cited

U.S. PATENT DOCUMENTS

| | | | |
|---|---|---|---|
| 3,054,284 A | | 9/1962 | Ciringione et al. |
| 3,208,266 A | * | 9/1965 | Black ........................ 73/9 |
| 3,512,612 A | * | 5/1970 | Bragg et al. ................ 188/378 |
| 3,693,402 A | | 9/1972 | Jones |
| 3,901,072 A | | 8/1975 | Vasiliev et al. |
| 3,955,400 A | * | 5/1976 | Parker ........................ 73/11.05 |
| 4,004,904 A | * | 1/1977 | Fergusson .................. 65/158 |
| 4,008,600 A | | 2/1977 | Bremer, Jr. et al. |
| 4,331,025 A | * | 5/1982 | Ord, Jr. ....................... 73/54.01 |
| 4,825,718 A | * | 5/1989 | Seifert et al. ............... 74/573.11 |
| 4,905,506 A | | 3/1990 | Lebershausen |
| 5,365,778 A | * | 11/1994 | Sheen et al. ................ 73/54.41 |
| 5,553,514 A | * | 9/1996 | Walkowc .................... 74/574.2 |
| 5,686,661 A | | 11/1997 | Singh et al. |
| 5,952,581 A | * | 9/1999 | Lammers et al. ............... 73/831 |
| 6,227,040 B1 | | 5/2001 | Hastings et al. |
| 6,446,494 B2 | | 9/2002 | Hastings et al. |
| 6,854,338 B2 | * | 2/2005 | Khuri-Yakub et al. ..... 73/861.27 |
| 6,907,361 B2 | * | 6/2005 | Molenaar et al. .............. 702/48 |

(Continued)

OTHER PUBLICATIONS

Hasse & Wrede GmbH, Viscous Torsional Vibration Dampers, 2007, pp. 1-2, SPG Media Limited http://www.ship-technology.com/contractors/noise/hasse-wrede/.

(Continued)

*Primary Examiner*—David A. Rogers
(74) *Attorney, Agent, or Firm*—Liell & McNeil

(57) ABSTRACT

A system for determining acceptability of torsional dampers for service in a machine system includes a fixture, an ultrasonic scanner and an indicating device configured to indicate at least one of acceptability and unacceptability of a torsional damper based upon receipt of a signal from the scanner. A nondestructive testing method for a torsional vibration damper includes scanning a torsional vibration damper with ultrasonic energy, and determining a test value for the damper indicative of a viscosity of fluid sealed within a housing of the damper based on receiving transmitted ultrasonic energy. Receipt of ultrasonic energy may be used to determine the flow rate of fluid within the damper by indicating a time for fluid to flow to fill a void within the damper. The system and method may be implemented in a remanufacturing or salvaging process for torsional vibration dampers.

18 Claims, 3 Drawing Sheets

U.S. PATENT DOCUMENTS

| | | | |
|---|---|---|---|
| 7,114,373 B2 * | 10/2006 | Hazelden et al. | 73/54.02 |
| 2001/0039830 A1 * | 11/2001 | Hastings et al. | 73/54.41 |
| 2007/0261499 A1 * | 11/2007 | Hamilton | 73/798 |

OTHER PUBLICATIONS

Metaldyne, Viscous Damper Repair, published prior to Apr. 24, 2007, p. 1, http://www.metaldyne.co.uk/viscous_damper_repair.html.

* cited by examiner

NONDESTRUCTIVE TESTING OF TORSIONAL VIBRATION DAMPERS

TECHNICAL FIELD

The present disclosure relates generally to analytical techniques and instruments, and relates more particularly to nondestructively testing and sorting of used torsional vibration dampers.

BACKGROUND

Torsional dampers are widely used in association with machine components, for example in the automotive, aerospace and construction industries. Many torsional dampers utilize a viscous damping fluid in conjunction with a relatively heavy rotatable "inertia" ring to damp a broad range of vibration frequencies of a rotating shaft. The fluid is typically sealed within a housing and transfers energy between the inertia ring and the rotating shaft to attenuate torsional vibrations. Utilizing a damper with sufficient fluid viscosity can be a critical factor in successful vibration damping. Over the course of many hours of service, high temperatures and shear forces can chemically and/or physically change the damping fluid such that viscosity is degraded. Consequently, performance of the damper suffers, potentially resulting in undue wear and tear on an associated rotating component, such as a crankshaft in an internal combustion engine.

It has become common in certain industries to scrap used dampers when a machine system, e.g. an engine, is disassembled for remanufacturing. Engineers have recognized for some time that viscous-fluid torsional dampers scrapped upon remanufacturing of the associated engine might still be serviceable. Challenges in separating acceptable dampers from those which are no longer serviceable, however, have inhibited widespread re-use of these components.

Several strategies exist for testing damper performance. On the one hand, dampers may be tested to determine performance by mounting the damper in a test rig and subjecting it to torsional vibrations. The relative effectiveness of the damper at attenuating the torsional vibrations can then be evaluated. While this approach may be worthwhile in some cases, it is quite labor intensive to mount torsional dampers within a test rig, then rotate the torsional damper and measure its damping abilities. Suitable damper testing rigs also tend to be expensive.

Viscosity of the damping fluid can also be tested directly. "Destructive" testing techniques have been used wherein a hole is drilled in a damper housing, and the viscosity of the fluid measured with a viscometer, or by some other means. This approach is also relatively labor intensive, and requires sophisticated resealing techniques for the damper housing, and care to avoid the introduction of contaminants into the fluid. None of the known strategies potentially available to evaluate torsional dampers for re-use has proven both satisfactory and cost effective, particularly for high volume remanufacturing and salvaging.

SUMMARY OF THE DISCLOSURE

The present disclosure provides a method of testing a torsional vibration damper including scanning a torsional vibration damper via ultrasonic energy. Scanning a torsional vibration damper includes transmitting ultrasonic energy toward the damper and receiving transmitted ultrasonic energy. The method further includes determining a test value for the damper indicative of a viscosity of fluid sealed within a housing thereof, based at least in part on receiving transmitted ultrasonic energy.

The present disclosure also provides a sorting process for used torsional dampers including scanning torsional dampers via ultrasonic energy. Scanning includes transmitting ultrasonic energy toward torsional dampers supported within a fixture, and receiving transmitted ultrasonic energy. The sorting process further includes determining values indicative of a viscosity of fluid sealed within a housing of each of the torsional dampers based at least in part on receiving transmitted ultrasonic energy. The sorting process still further includes sorting each one of the torsional dampers into one of a plurality of categories based on the determined values.

The present disclosure also provides a system for determining acceptability of torsional dampers for service in a machine system including a fixture configured to support a torsional damper at a fixed orientation free of torsional vibrations. The system further includes a scanner operable to scan a torsional damper within the fixture, the scanner including an ultrasonic transmitter and an ultrasonic receiver. The ultrasonic receiver is configured to output a signal indicative of a viscosity of fluid within the torsional damper. The system still further includes an indicating device configured to receive the signal and responsively indicate at least one of acceptability and unacceptability of a torsional damper within the fixture.

DETAILED DESCRIPTION

Figure 1:
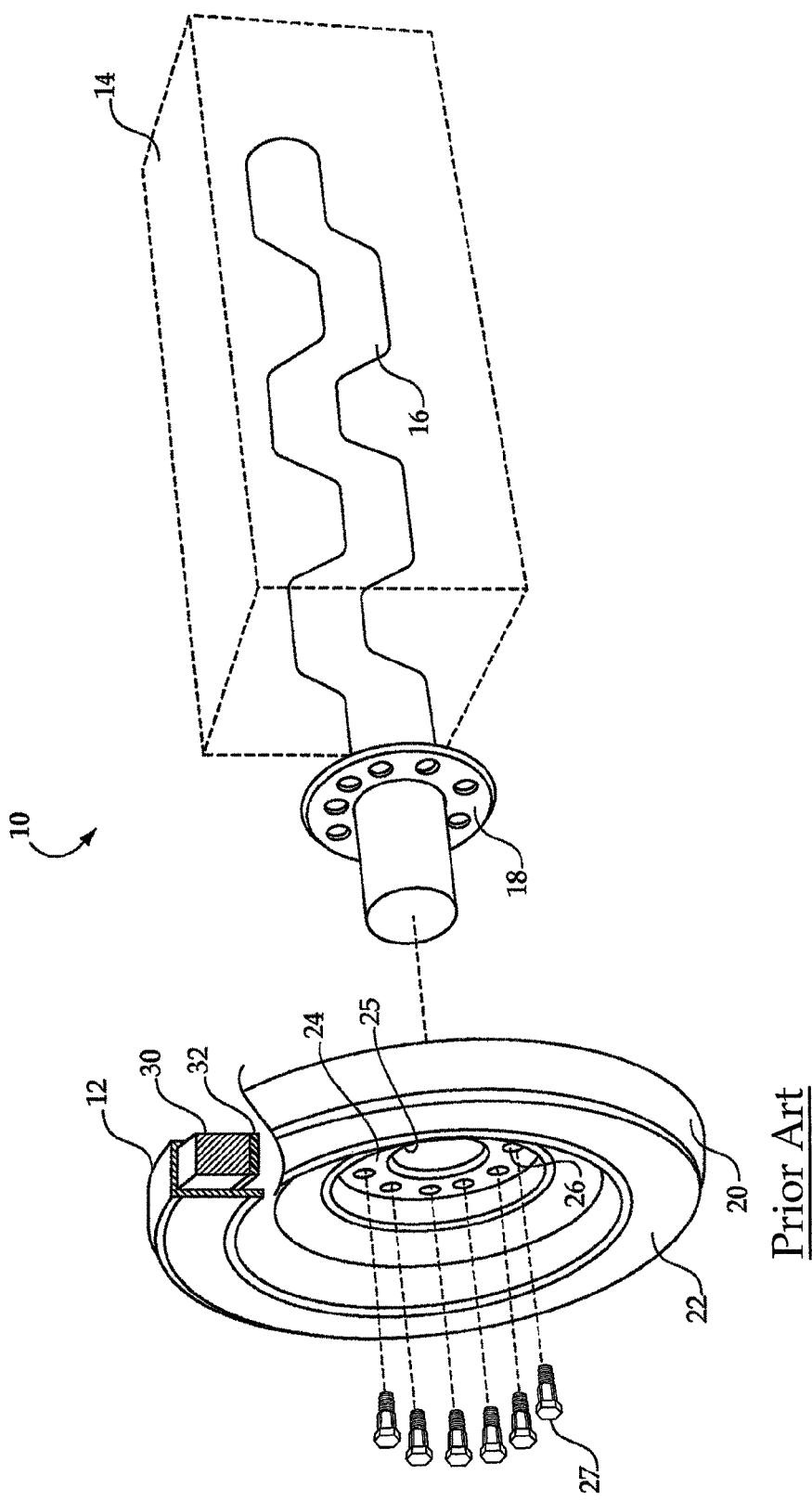
FIG. 1 is an exploded, partially sectioned view of a machine system that includes a torsional damper.

Referring to FIG. 1, there is shown a machine system 10 including a machine housing 14 having a rotatable shaft 16 coupled therewith. Shaft 16 includes a coupling plate 18 mounted thereon which is adapted to couple with a rotary torsional damper 12. Damper 12 is used herein in connection with a description of exemplary sorting methods, etc., according to the present disclosure. It should be appreciated that the structure of damper 12 which is shown is illustrative only, and the present disclosure is applicable to other damper types. Damper 12 may include a mounting plate 24 having a central aperture 25 surrounded by a plurality of holes 26. A plurality of bolts 27 are positionable through holes 26 to engage with plate 18 for coupling damper 12 therewith. Damper 12 may further include a housing 20 having a cover plate 22, and an inertia ring 30 positioned therein. Inertia ring 30 may be rotatable relative to housing 20 and positioned upon a bearing 32, such as a PTFE ring. A viscous damping fluid is sealed within housing 20, transferring rotational energy between shaft 16 and inertia ring 30 to enable damping of torsional vibrations of shaft 16 in a conventional manner. As further described herein, a technique and system for nondestructively evaluating the acceptability of dampers such as damper 12 for use in a machine system is provided. It is contemplated that one practical implementation of the to be described evaluation technique and system will be in the field of remanufacturing and salvaging. Used torsional dampers may thus be tested and sorted in the manner described herein to separate those dampers which are no longer effective, or otherwise unsuitable, from those dampers which may be returned to service. It should be appreciated, however, that while remanufacturing and salvaging is contemplated to be a principal application, the present disclosure is not thereby limited, and the teachings set forth herein might advantageously be applied to testing, sorting, etc. of dampers prior to initial use.

One specific application of the present disclosure will be the evaluation of torsional dampers removed from service in an engine system. To this end, machine system 10 might comprise an engine system wherein machine housing 14 is an engine housing and shaft 16 is a crankshaft. Those skilled in the art will appreciate, however, the broad applicability of the present disclosure in evaluating torsional dampers used in other machine environments. For instance, rather than an internal combustion engine system, the present testing, sorting and system concepts might be applied to dampers used with a wide variety of torque transmitting shafts such as driveshafts for mobile machines, propeller driveshafts, compressor, pump and turbine shafts, etc.

Figure 5:
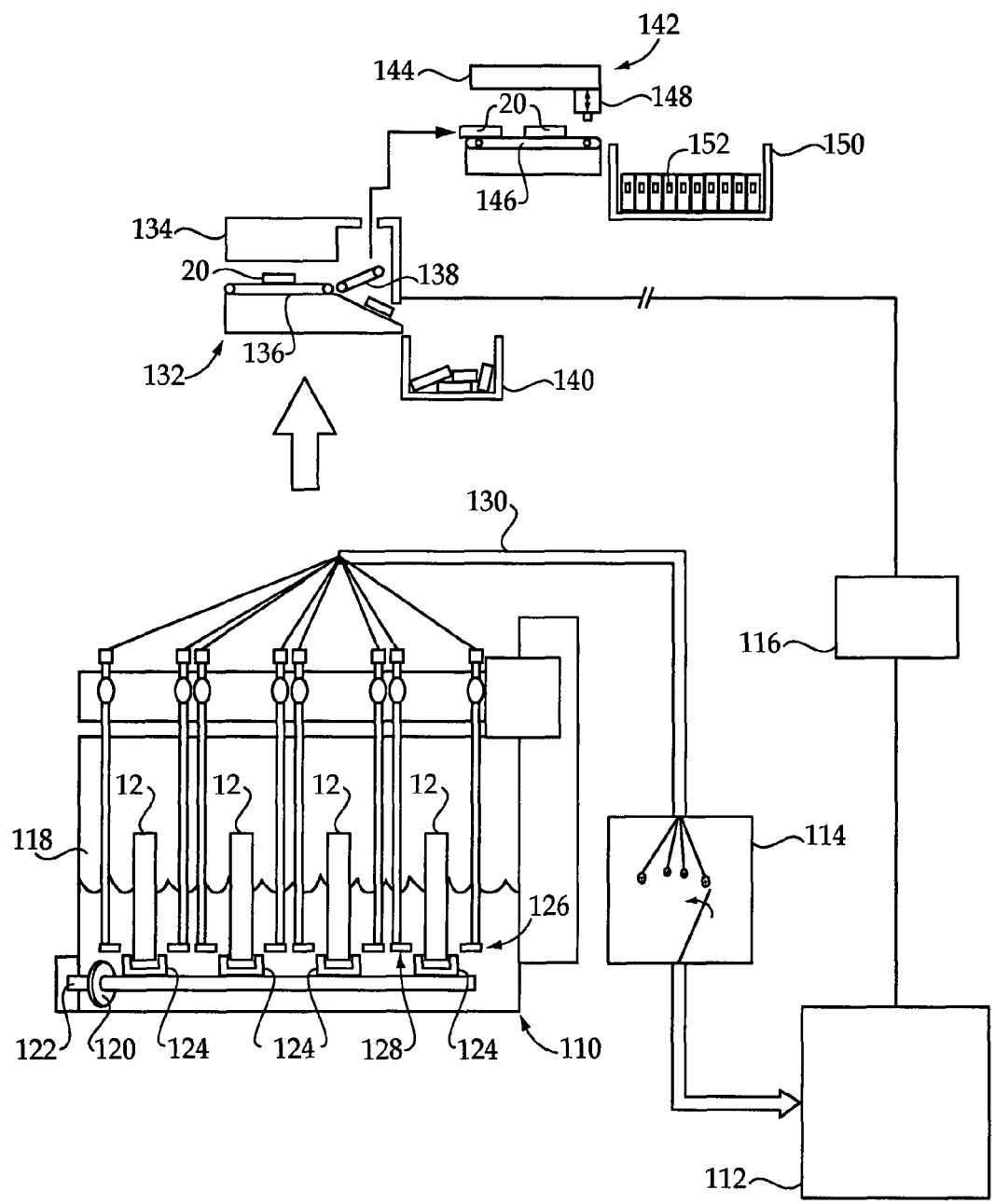
FIG. 5 is a schematic view of a torsional damper testing and salvaging system according to one embodiment.

Turning now to FIG. 5, there is shown schematically a system 100 such as might be used in remanufacturing machine systems, and in particular evaluating and sorting dampers used therein based on their acceptability/suitability for further service. System 100 may include a testing apparatus 110, wherein one or more torsional dampers 12 may be tested to determine whether they are acceptable for further service. Apparatus 110 may include a fluid tank 118 and a fixturing device or "fixture" 120, which is configured to support one or more torsional dampers free of torsional vibrations within a fluid in tank 118. Fixturing device 120 may include a plurality of support elements 124 corresponding to a number of torsional dampers which apparatus 110 is capable of testing. Fixturing device 120 may also include an actuator 122 operable to adjust dampers 12 from a first fixed orientation to a second fixed orientation, for example by rotating, the significance of which will be apparent from the following description.

Apparatus 110 may also be equipped with a plurality of scanners, each comprising an ultrasonic transmitter 126 and an ultrasonic receiver 128. Each ultrasonic transmitter 126 and ultrasonic receiver 128 may comprise a signal transducer configured to convert an electrical signal to and from an ultrasonic signal, respectively. A plurality of communication lines, shown via reference number 130, are connectable with a computer 112 via a selector device 114. In one embodiment, selector device 114 is configured to selectively connect each paired set of one transmitter 126 and one receiver 128 to computer 112 for selectively scanning each damper 12 individually. In other embodiments, all of dampers 12 could be scanned simultaneously, as sub-groups, etc.

Computer 112 may be configured to determine a test value for each of the individual dampers which is indicative of a viscosity of a damping fluid sealed within a housing thereof. As further described hereinbelow, receiving transmitted ultrasonic energy with each receiver 128 may provide an indication of fluid viscosity within each damper 12. Computer 112 may further associate a determined test value with each individual damper 12 based on receiving transmitted ultrasonic energy with one of receivers 128. In other words, each individual damper 12 may be assigned a test value used for sorting, marking, etc., further described herein.

System 100 may further include an indicating device 116 which is configured to receive a signal from each receiver 128 or computer 112, corresponding to a test value for one of dampers 12. Responsive to receipt of the signals, indicating device 116 may indicate at least one of, acceptability and unacceptability, of torsional dampers in test apparatus 110 for further service. In other words, indicating device 116 may be operable to indicate which dampers are unacceptable, based on a determined test value corresponding therewith, or indicating device 116 could indicate which of the dampers are acceptable based on the determined test value. Further still, indicating device 116 might indicate both acceptable and unacceptable dampers in a sampled set of dampers.

In one embodiment, indicating device 116 could comprise a light, with its color or illumination state indicating acceptability, unacceptability, etc. of dampers 12 tested with test apparatus 110. In other embodiments, indicating device 116 might indicate acceptability or unacceptability by outputting a control signal to a sorting apparatus 132, further described herein. In still other embodiments, indicating device 116 might consist of a component of computer 112, rather than a separate system component. Indicating device 116 will typically have at least two states, corresponding to acceptable versus unacceptable dampers. It should thus be appreciated that indicating device 116 need not take any particular action other than generating an operator or machine perceptible signal that can enable an operator or machine to sort dampers 12 based on whether they are determined to be acceptable, unacceptable, etc.

Where sorting apparatus 132 is used, dampers 12 might be transferred from testing apparatus 110 to a conveyor 136 mounted to a housing 134 of sorting apparatus 132. Sorting apparatus 132 might further include a second conveyor 138 or some other suitable element such as a gate which can direct dampers determined to be unacceptable to a scrap bin 140, and direct dampers determined to be acceptable elsewhere for further processing. Sorting apparatus 132 may be controllably coupled with indicating device 116 such that indicating device 116 outputs control signals thereto which control a position, etc. of element 132 for sorting of dampers 12.

Dampers having test values corresponding to acceptability may be further processed by marking them accordingly. To this end, a marking apparatus 142 may be provided which includes a housing 144 and a conveyor 146 operable to convey acceptable dampers 20 past a marking device 148. Dampers conveyed past marking apparatus 142 may have a label 152 affixed thereon. Marked dampers may then be placed in a storage bin 150 for eventual returning to service in a machine system. It should be appreciated that rather than affixing a label 152, some other marking means may be used for either of acceptable dampers or unacceptable dampers, or both, to enable a technician or machine to further process the dampers. For instance, rather than a label, some type of paint, barcode, or other means for marking might be used.

It should be appreciated that system 100 is exemplary only, and a wide variety of systems for determining acceptability or unacceptability, or both, of torsional dampers might be used without departing from the intended spirit and scope of the present disclosure. For example, testing apparatus 110, sorting apparatus 132 and marking apparatus 142 might all be part of an integrated processing machine operable to test, sort and mark dampers 12 accordingly. In other embodiments, rather than using a sorting apparatus to sort dampers based on a signal from indicating device 116, dampers might be marked via apparatus 142 or another suitable apparatus responsive to a control signal from indicating device 116. Marked dampers could later be sorted manually or via machine based on the markings thereon. It should also be appreciated that marking of dampers 12 need not be undertaken at all, but rather used dampers 12 evaluated with testing apparatus 110 might simply be sorted to one of a scrap bin or a salvage bin.

As will be further apparent from the following description, a practical implementation strategy may be determining that a given damper is either acceptable, or unacceptable, based on whether its associated fluid viscosity is above a reference viscosity. In general, it has been discovered that dampers which are otherwise acceptable, e.g. free of housing structural damage, leaks, etc. may be returned to service in a similar application from which they have been removed, so long as their damping fluid is of a sufficient viscosity. In other words, for at least certain damper types, they can either be expected to operate acceptably, or not, depending of course upon the particular machine environment. It may be desirable in certain instances to subject dampers 12 to a pre-scanning or post-scanning inspection process to determine whether some failure mode other than reduced fluid viscosity has occurred, or is likely to occur. As mentioned above, in some instances dampers 12 may develop leaks in their respective housing 20. It will typically be desirable to sort leaking dampers to scrap rather than scanning them. Similarly, dampers which exhibit damage to their housing 20, such as damage to bolt holes 26, plate 24 or aperture 25 might be scrapped rather than scanned. Alternatively, inspection for failure modes unrelated to fluid viscosity might take place after scanning dampers 12 if desired.

As mentioned above, testing apparatus 110, or another suitable testing apparatus, may be used to determine a test value for each damper 12 which is indicative of a viscosity of fluid sealed within the housing 20 thereof. In general, it will be desirable to compare the determined test values with a reference value corresponding, for example, to a minimum acceptable fluid viscosity. If a determined test value is equal to or greater than the reference value, or within an acceptable tolerance thereof, then the corresponding damper 12 may be determined to be acceptable for returning to service. The reference value might consist of an empirically determined value corresponding to fluid viscosity. For instance, one or more dampers might be mounted in a test rig(s) and their capacity to damp torsional vibrations evaluated. Numerous types of damper testing rigs and systems are known to those skilled in the art. Dampers known to have acceptable damping ability could then be tested via apparatus 110 to determine reference values for viscosity of their damping fluid which can serve as the standard to which subsequently tested dampers are compared. Rather than calibrating test apparatus 110 via tests of acceptable dampers on a test rig, then determining test values associated therewith, fluid known to have suitable viscosity might be placed in a damper, and its flow rate then determined to arrive at a reference value for comparison with dampers tested during a salvaging/sorting operation. Other known analytical techniques to determine a fluid viscosity and corresponding reference value associated with acceptable damper operation might be used.

Another practical method of determining reference values may include placing one or more used dampers in an oven or the like to heat the damper(s) and induce thermal degradation of the damping fluid therein, simulating conditions a damper might experience in use. For example, identical dampers might be subjected to varying durations of oven treatment or varying temperatures. Once the dampers have been subjected to oven heating, they may be analyzed with system 110, to determine/infer a flow rate of fluid sealed therein. By utilizing system 110 in the manner described herein, a number can be assigned to each oven-treated damper, yielding different numbers/values based on the duration, oven temperature or other variables relating to oven treatment, the different numbers corresponding to different viscosities of fluid therein. The viscosity of fluid in these dampers can then be measured directly, and compared with viscosity of fluid from a new damper. Oven treated dampers having fluid which has lost more than a threshold degree of viscosity, as compared with fluid from the new damper, may thus be used to provide the reference value. During testing/sorting of dampers as contemplated herein, dampers having test values equal or similar to the reference value(s) associated with the unsuitable dampers can be sorted to scrap, etc. It should further be appreciated that a variety of torsional damper types are known in the art and are used in a variety of machine sizes and system types, using damping fluid of varying viscosity. It may accordingly be desirable in some instances to calibrate system 100 to a given type of damper or type of damping fluid.

INDUSTRIAL APPLICABILITY

Remanufacturing of machine systems removed from service such as machine system 10 of FIG. 1 may begin by disassembling machine system 10 and removing damper 12 from engagement with plate 18. A plurality of machine systems will often be received together for remanufacturing or component salvaging, and testing of dampers 12 may not begin until a certain minimum number has been received. When one or more dampers 12 are to be tested, they may be placed in apparatus 110 and supported at a first fixed orientation via fixturing device 120, at least partially submerged in fluid in tank 118.

Several different means for determining test values indicative of fluid viscosity for dampers 12 are contemplated herein. One practical implementation strategy includes determining a test value based on a fluid flow rate within the damper housings 20, while maintaining the housings 20 in a sealed state. In contrast to earlier strategies it is not necessary within the context of the present disclosure to unseal or otherwise open a damper housing to determine, estimate or infer a viscosity of the fluid therein. In one embodiment, fluid flow rate may be determined by positioning dampers 12 at the first, fixed orientation for at least a minimum predetermined period of time, to permit a void to form within their respective housings 20. When dampers 12 are positioned at the first fixed orientation, damping fluid in the corresponding housing 20 of each damper 12 will have a tendency to flow entirely, or almost entirely, to one end of the corresponding housing 20, creating a void at the opposite end thereof. Fluid tends to flow in the described manner under the force of gravity, essentially forming a bubble that comprises the void. In general, most viscous-fluid torsional dampers will be less than fully filled to accommodate volumetric changes in the viscous fluid in response to temperature changes. This extra space enables formation of a void toward one end of each housing when dampers 12 are positioned at a fixed orientation for a sufficient time.

After positioning the dampers at the first fixed orientation for a period of time sufficient to allow the voids to form, they may be reoriented to a second, fixed orientation to induce fluid flow into the respective voided portions of housings 20. In other words, when reoriented the void which was formerly at the top of each damper is moved to the bottom. Typically, reorienting dampers 12 will take place without inducing rotation of their inertia rings relative to their housings. Determining a time of refilling, or partially refilling, the voided portions allows a relative flow rate of fluid in each of dampers 12 to be determined. Since fluid flow rate corresponds to fluid viscosity, the determined flow rate, as indicated by the test value associated with a given damper, can indicate acceptability or unacceptability of the corresponding damper 12 for further service.

Thus, reorienting each damper 12 via fixturing device 120 of test apparatus 110, or another suitable apparatus, will result in moving of the fluid void to a different part of the housing 20 of each damper 12. After reorienting each of the dampers 12, a portion of each damper 12 may be scanned with ultrasonic energy via transmitting ultrasonic energy with each transmitter 126, and receiving ultrasonic energy with each receiver 128. It has been discovered that an ultrasonic signature for ultrasound transmitted through voided portions of the housings 20 will differ from an ultrasonic signature associated with the voided portions once refilled with fluid. In other words, ultrasonic energy received with each receiver 128 will differ, depending upon whether fluid is present in the voided portions.

Figure 2:
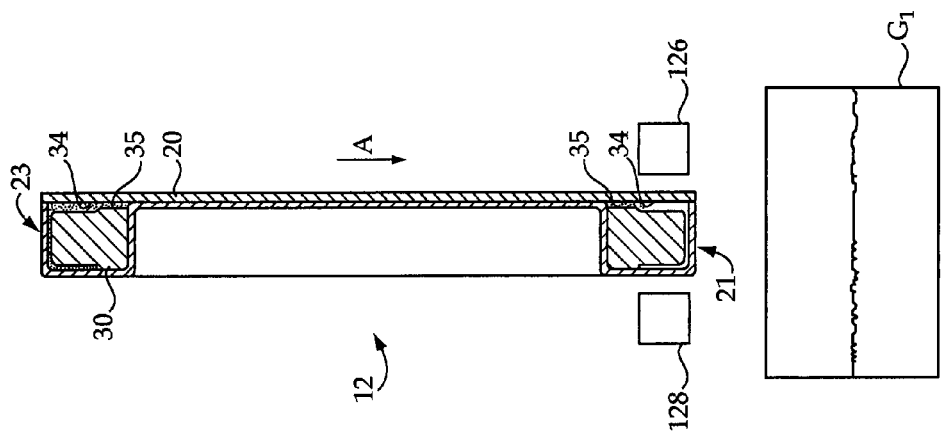
FIG. 2 is a sectioned side view of a torsional damper, and a graph corresponding to an ultrasonic scan through a portion of the damper substantially voided of fluid.

Turning now to FIG. 2, there is shown a sectioned side view of a damper 12 wherein a damping fluid 35 is disposed predominantly towards one end 23 of a housing 20. Damper 12 is illustrated as it might appear just after being reoriented to the second fixed orientation, for example reoriented 180° from the first orientation. It will be noted that a gap 34 exists between a portion of housing 20 and inertia ring 30. Gap 34 will typically comprise an annular gap extending all the way around the interface between housing 20 and inertia ring 30, as shown in cross-section in FIG. 2, and hence overlapping the voided portion at end 21. Once reoriented, fluid 35 will begin to flow downward under the force of gravity, generally in a flow direction shown via arrow A, towards end 21 of housing 20. As fluid leaves housing 20 close to end 23, a new void will tend to form at end 23.

Also shown in FIG. 2 are an ultrasonic transmitter 126 and an ultrasonic receiver 128 positioned such that when damper 20 is initially reoriented, a voided portion of annular gap 34 lies between transmitter 126 and receiver 128. Also shown in FIG. 2 is a graph $G_1$ illustrating an ultrasonic signal signature corresponding with ultrasonic energy that might be expected to be received via receiver 128 when the voided portion of annular gap 34 is scanned. It will be noted that little or no ultrasound is received via receiver 128 when the conditions in damper 12 are as shown in FIG. 2, as ultrasound will typically be poorly transmitted, if at all, across the voided portion of gap 34 at end 21.

Figure 3:
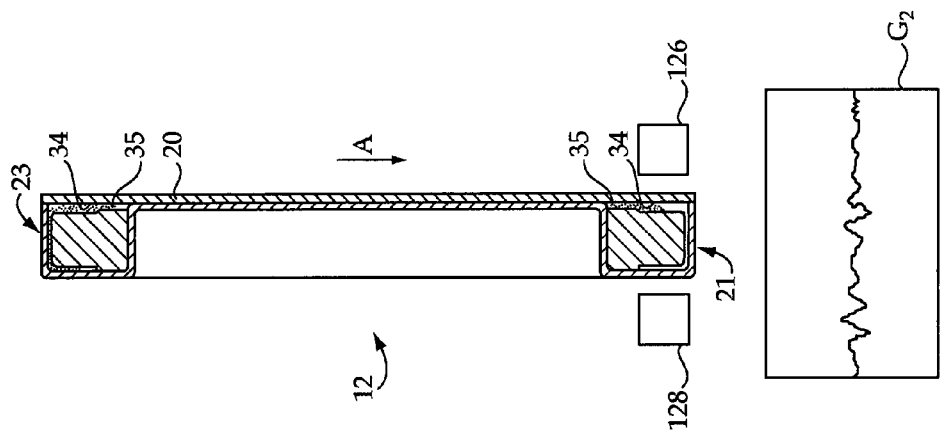
FIG. 3 is a sectioned side view of a torsional damper, and a graph corresponding to an ultrasonic scan through a portion of the damper partially filled with fluid.

Turning now to FIG. 3, there is shown damper 12 after it has been positioned at its second, fixed orientation for a period of time sufficient that fluid 35 has begun to accumulate at end 21 of housing 20. It will be noted that some of fluid 35 is within annular gap 34, at end 21, but some of fluid 35 remains at or close to the portion of annular gap 34 at second end 23 of housing 20. Also shown in FIG. 3 is a graph $G_2$ illustrating an ultrasonic signal signature that might be expected when fluid has begun to flow into the voided portion of housing 20 adjacent end 21.

Figure 4:
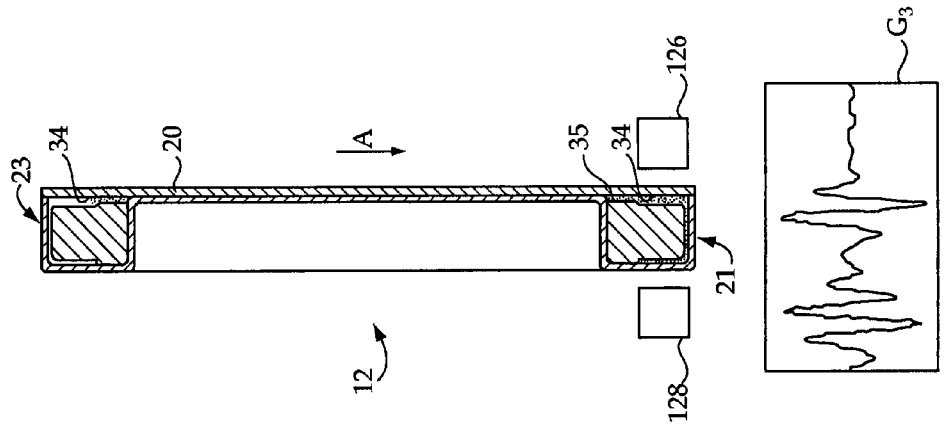
FIG. 4 is a sectioned side view of a torsional damper, and a graph corresponding to an ultrasonic scan through a portion of the damper substantially filled with fluid.

Referring to FIG. 4, there is shown damper 20 approximately as it might appear after fluid 35 has substantially filled the portion of annular gap 34 adjacent end 21 of housing 20. It may also be noted in FIG. 4 that the portion of annular gap 34 adjacent housing end 23 is substantially or entirely devoid of fluid 35. Also shown in FIG. 4 is graph $G_3$ illustrating the relatively strong ultrasonic signal signature that might be expected when fluid has substantially or entirely filled the portion of annular gap 34 adjacent end 21 of housing 20.

The series of graphs and fluid locations within housing 20 shown in FIGS. 2-4 illustrates the different ultrasonic signal amplitudes that might be expected when ultrasound is transmitted toward a void, a partially filled void, and through fluid, respectively. To determine a flow rate of fluid within housing 20, a time duration between initially reorienting damper 12, approximately as shown in FIG. 2, and receipt of a maximum amplitude ultrasonic signal, or a signal corresponding to any other predetermined fill state of the scanned volume, approximately as shown in FIG. 4, may be measured. This time duration can then be compared with a reference time to arrive at a test value indicative of a viscosity of fluid within housing 20. Dampers wherein the fluid is not sufficiently viscous could be detected where a signal pattern shown in graph $G_3$ arises relatively more quickly, corresponding to fluid flow through housing 20 more rapidly than that expected for suitably viscous fluid. Alternative strategies are contemplated wherein, rather than reorienting damper 12 180°, damper 12 is reoriented less than or more than 180°, and a corresponding region of gap 34 scanned.

The present disclosure thus provides a relatively simple, straightforward and nondestructive technique for determining whether fluid within housing 20 of damper 12 is insufficiently viscous and the associated damper 12 therefore not acceptable for returning to service. While inferring fluid flow rate as described herein is contemplated to be one practical implementation strategy, the present disclosure is not limited to this specific technique.

The present description is for illustrative purposes only, and should not be construed to narrow the breadth of the present disclosure in any way. Thus, those skilled in the art will appreciate that various modifications might be made to the presently disclosed embodiments without departing from the full and fair scope of the present disclosure. Other aspects, features and advantages will be apparent from an examination of the attached drawings and appended claims.

We claim:

1. A method of testing a torsional vibration damper comprising:
   scanning a torsional vibration damper via ultrasonic energy, including transmitting ultrasonic energy toward the damper and receiving transmitted ultrasonic energy;
   determining a test value for the damper indicative of a viscosity of fluid sealed within a housing thereof, based at least in part on receiving transmitted ultrasonic energy; and
   wherein scanning a torsional vibration damper further includes scanning a portion of the torsional vibration damper that includes a void formed within the housing as a result of flow of the fluid under the force of gravity.

2. The method of claim 1 wherein determining a test value further comprises determining a fluid flow rate within the housing while maintaining the housing in a sealed state.

3. The method of claim 2 further comprising permitting the void to form within the housing, wherein determining a fluid flow rate within the housing further comprises determining a timing of filling the void with fluid.

4. The method of claim 3 wherein permitting the void to form comprises positioning the damper at a first orientation, the method further comprising inducing fluid flow into the void by reorienting the damper to a second, different orientation after permitting a void to form.

5. The method of claim 4 wherein the damper includes an inertia ring movable relative to the housing and an annular gap between the inertia ring and the housing, wherein permitting the void to form includes permitting a void to form that includes a portion of the annular gap, and wherein scanning the damper includes transmitting ultrasonic energy through the gap and receiving ultrasonic energy transmitted through the gap.

6. The method of claim 5 wherein determining a timing of filling the void with fluid further comprises determining a timing of filling based at least in part on an amplitude of received ultrasonic energy.

7. The method of claim 4 wherein the damper includes an inertia ring movable relative to the housing, and wherein inducing fluid flow into the void comprises rotating the damper about 180° from the first orientation without rotating the inertia ring relative to the housing.

8. A sorting process for used torsional dampers comprising:
scanning torsional dampers via ultrasonic energy, including transmitting ultrasonic energy toward torsional dampers supported within a fixture and receiving transmitted ultrasonic energy;
determining values indicative of a viscosity of fluid sealed within a housing of each of the torsional dampers based at least in part on receiving transmitted ultrasonic energy;
sorting each one of the torsional dampers into one of a plurality of categories based on the determined values; and
wherein scanning torsional dampers further includes scanning a portion of each one of the torsional dampers that includes a void formed within the housing thereof as a result of flow of the fluid under the force of gravity.

9. The sorting process of claim 8 further comprising associating the determined values with the torsional dampers.

10. The sorting process of claim 9 further comprising marking at least a portion of the torsional dampers in accordance with the determined values.

11. The sorting process of claim 8 further comprising placing a group of dampers in a fixture, and filling the corresponding void with fluid at least in part by reorienting the group of dampers in the fixture prior to scanning via ultrasonic energy.

12. The process of claim 11 wherein determining values comprises determining a timing at which each of the voids reaches a predetermined fill state after reorienting the dampers.

13. The process of claim 12 further comprising maintaining the group of dampers at a first orientation within the fixture for a predetermined minimum time prior to reorienting the group of dampers.

14. The process of claim 8 wherein sorting each one of the dampers further comprises sorting dampers to an acceptable category where a determined value associated therewith corresponds to a relatively higher viscosity, and sorting dampers to an unacceptable category where a determined value associated therewith corresponds to a relatively lesser viscosity.

15. The process of claim 14 further comprising permitting the void to form in housings of each of the dampers and inducing fluid flow within each of the housings after permitting the void to form, wherein determining values includes determining values indicative of whether fluid is present in the voids at a time subsequent to inducing fluid flow.

16. The process of claim 14 wherein the dampers comprise engine crankshaft dampers having a central aperture and a plurality of mounting holes radially about the central aperture, the process further comprising:
receiving a plurality of engine crankshaft dampers removed from service in a plurality of engine systems;
inspecting each of the plurality of dampers for damage prior to scanning via ultrasonic energy; and
sorting less than all of the plurality of dampers to the unacceptable category without scanning them via ultrasonic energy, based at least in part on inspecting the dampers for damage.

17. A system for determining acceptability of torsional dampers for service in a machine system comprising:
a fixture configured to support a torsional damper at a fixed orientation free of torsional vibrations;
a scanner operable to scan a torsional damper within said fixture, said scanner including an ultrasonic transmitter and an ultrasonic receiver configured to output a signal indicative of a viscosity of fluid within the torsional damper;
an indicating device configured to receive said signal and responsively indicate at least one of acceptability and unacceptability of a torsional damper within said fixture;
wherein said indicating device has at least two different states and wherein said system further comprises a sorting device configured to sort torsional dampers based on a state of said indicating device; and
a tank, said fixture being configured to support a plurality of torsional dampers and having at least one actuator configured to adjust said plurality of torsional dampers between a first orientation and a second, scanning orientation within said tank, said second orientation comprising said fixed orientation.

18. The system of claim 17 further comprising means for determining a value indicative of a flow rate of fluid within a damper within said fixture based at least in part on said signal.

* * * * *